United States Patent [19]

Germanaud et al.

[11] Patent Number: 5,021,175
[45] Date of Patent: Jun. 4, 1991

[54] ADDITIVES TO LUBRICATING OILS HAVING EXTREME PRESSURE, ANTIWEAR AND ANTIOXIDANT EFFECTS, PROCESS FOR PREPARATION THEREOF AND LUBRICATING COMPOSITIONS CONTAINING SAID ADDITIVES

[75] Inventors: Laurent Germanaud, Irigny; Robert Nouguier, Plan de Cuques, both of France

[73] Assignee: Elf France, Paris, France

[21] Appl. No.: 593,462

[22] Filed: Oct. 4, 1990

Related U.S. Application Data

[63] Continuation of Ser. No. 341,574, Apr. 21, 1989, abandoned.

[30] Foreign Application Priority Data

Jun. 5, 1988 [FR] France .................. 88 06091

[51] Int. Cl.$^5$ .................. C10M 137/10; C10M 137/14
[52] U.S. Cl. .................... 252/46.6; 558/151
[58] Field of Search .................. 252/46.6; 558/151

[56] References Cited

U.S. PATENT DOCUMENTS

| | | | |
|---|---|---|---|
| 3,035,082 | 5/1962 | Lorenz | 558/151 |
| 3,109,770 | 11/1963 | Price et al. | 558/151 |
| 3,144,384 | 8/1964 | Aichenegg | 558/151 |
| 3,309,428 | 3/1967 | Calhoun et al. | 558/151 |
| 3,742,099 | 6/1973 | Colclough et al. | 558/151 |
| 3,763,284 | 10/1973 | Phillips | 558/151 |

FOREIGN PATENT DOCUMENTS

| | | | |
|---|---|---|---|
| 252969 | 2/1963 | Australia | 558/151 |
| 251635 | 4/1963 | Australia | 558/151 |
| 681839 | 3/1964 | Canada | 558/151 |
| 949083 | 2/1964 | United Kingdom | 558/151 |

*Primary Examiner*—Prince E. Willis
*Assistant Examiner*—E. McAvoy
*Attorney, Agent, or Firm*—Burgess, Ryan & Wayne

[57] ABSTRACT

Lubricating oil additives are provided which have extreme pressure, antiwear and antioxidant properties. The additives are dithiophosphorous disymmetric bisulphides of the formula:

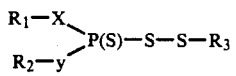

wherein X and Y represent an oxygen or sulphur atom or a methylene group and $R_1$ and $R_2$ and $R_3$ represent a hydrocarbon radical, a polyether, a polythioether or a hydrogen atom.

The invention also relates to a process for their preparation and to lubricating compositions containing the additives.

6 Claims, No Drawings

ADDITIVES TO LUBRICATING OILS HAVING EXTREME PRESSURE, ANTIWEAR AND ANTIOXIDANT EFFECTS, PROCESS FOR PREPARATION THEREOF AND LUBRICATING COMPOSITIONS CONTAINING SAID ADDITIVES

This application is a continuation of application Ser. No. 341,574, filed Apr. 21, 1989, now abandoned.

BACKGROUND OF THE INVENTION

(1) Field of the Invention

This invention relates to additives for lubricating oils having extreme pressure, antiwear and antioxidant properties. In one aspect, this invention is directed to additives for lubricating oils which are thiophosphorous, disymmetric bisulfides. As a further aspect, this invention relates to a process for the preparation of the additives as well as lubricating compositions containing such additives.

(2) Description of the Related Art

It is known to add additives to lubricating oils for improving the resistance to oxidation and wear of such oils. Thus, the zinc dialkyldithiophosphates such as those described in U.S. Pat. Nos. 4,436,400; 4,466,895; 4,587,062 and in Belgian Patent 896,226 have an antiwear and antioxidant effect. But those additives lose their effectiveness when the lubricated metal parts are subjected to high stresses. Therefore, they cannot be used as extreme-pressure additives. Besides, these metal salts in certain cases interact with the dispersants having a base of amines or polyamines thus altering the antiwear properties of the dithiophosphates. In addition, the presence of metals can lead to the appearance of ashes which counteracts the effect sought.

Unlike the above, another kind of additive, the polysulphurated olefins described, for example, in U.S. Pat. Nos. 4,097,387; 4,119,545; 4,119,550 and 4,198,305, can be used in conditions of extreme pressure. These products are good antiwear and extreme-pressure addditives, but they have no antioxidant effect.

An additive has now been found for lubricating oils which has at the same time, an antiwear, antioxidant and extreme-pressure effect.

SUMMARY OF THE INVENTION

The additive according to the invention is characterized in that it is comprised of a thiophosphorous disymmetric bisulphide corresponding to the general formula:

$$\begin{matrix} R_1-X \\ \phantom{R_1-X} \diagdown \\ \phantom{R_1-XX} P(S)-S-S-R_3 \quad (I) \\ \phantom{R_1-X} \diagup \\ R_2-Y \end{matrix}$$

wherein X and Y, identical or different, represent an oxygen or sulphur atom or a methylene group.

If X and Y represent an oxygen or a sulphur atom, $R_1$, $R_2$ and $R_3$, can be identical or different, and represent a saturated, unsaturated, or aromatic, acyclic or cyclic, hydrocarbon radical or a chain of the general formula:

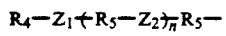

wherein $Z_1$ and $Z_2$, can be identical or different and correspond to an oxygen or sulphur atom, $R_4$ corresponds to an alkyl group, $R_5$ corresponds to an alkylene group and n is comprised between 0 and 8.

If X and Y represent a methylene group, $R_1$ and $R_2$, can be identical or different, and represent a hydrogen atom or a hydrocarbon radical and $R_3$ represents a hydrocarbon radical as described above.

If X and Y represent oxygen or sulphur atoms, $R_1$ and $R_2$ are in general alkyl groups, saturated or aromatic rings, or chains of the general formula:

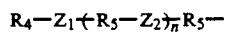

The alkyl groups $R_1$ and $R_2$ are in general composed of from $C_1$ to $C_{22}$, preferably from $C_1$ to $C_{12}$, or more preferably from $C_1$ to $C_8$.

The saturated or aromatic rings are in general composed of from $C_5$ to $C_6$, preferably $C_6$. These rings can be substituted or not.

In the general formula

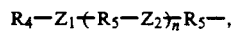

$Z_1$ and $Z_2$ preferably correspond to an oxygen atom, $R_4$ corresponds to an alkyl group of from $C_1$ to $C_{12}$ and preferably of $C_1$ to $C_6$, $R_5$ corresponds to an alkylene group of from $C_2$ to $C_4$ and n is from between 0 and 8, preferably, between 0 and 3.

If X and Y correspond to methylene groups, $R_1$ and $R_2$ correspond in general to hydrogen or an alkyl group of from $C_1$ to $C_{21}$, preferably of from $C_1$ to $C_{11}$, or more preferably, $C_1$ to $C_5$.

Independently of the nature of X and Y, $R_3$ corresponds in general to a saturated or unsaturated alkyl group of from $C_1$ to $C_{12}$, preferably $C_1$ to $C_6$, more preferably, $C_2$ to $C_4$, or an aralkyl group.

$R_3$ is selected preferably among the n-propyl, n-butyl, iso-butyl, allyl, methallyl, or benzyl groups.

The additives of general formula (I) wherein X and Y correspond to oxygen, that is, the O,O-diesters of dithiophosphoric acid, are preferred.

DETAILED DESCRIPTION OF THE INVENTION

There exist several processes for preparing compounds of the general formula (I). U.S. Pat. Nos. 3,109,770 and 4,496,683 describe the reaction of a sodium dialkyl dithiophosphate with an alkylsulphenyl halide or also the reaction of a dialkyldithiophosphoryl sulphenyl halide with a sodium mercaptoate. This method requires the preparation of the sulphenyl halide as an intermediary, a highly toxic product.

U.S. Pat. Nos. 3,705,293; 3,859,297; 4,006,155 and 4,119,780 refer to the reaction of a compound having -SH function(s), as for example, a dialkyldithiophosphoric acid with a sulphenamide such as N(alkylthio)phthalamide. Here, the intermediary sulphanamide is also a toxic and corrosive product.

U.S. Pat. No. 3,035,082 discloses the preparation of products of the general formula (I) by condensation of a dialkyldithiophosphoric acid on an S-alkylthiosulphate in aqueous phase. The products have to be extracted from the aqueous phase by an organic solvent and the yield of this synthesis does not exceed 50 to 60%.

The process of the invention makes it possible to avoid the extraction stage and at the same time to increase considerably the yield of this synthesis.

The process of synthesis of bisulphides of the general formula (I) comprises the condensation of a compound of the general formula:

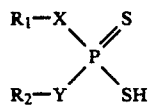

with an S-alkylthiosulphate of the general formula $$R_3—S—SO_3M \qquad (III)$$

wherein $R_1$, $R_2$, $R_3$, X and Y have the values indicated above and M represents an alkaline, alkaline earth metal, or an ammonium ion, characterized in that the condensation takes place in a two phase medium including water and an organic solvent in the presence of a phase transfer agent.

The synthesis of the compounds of general formula (II) is known already having been described, for example, in the work: ORGANOPHOSPHORUS COMPOUNDS BY G. M. KOSOLAPOFF (John Wiley, 1950, New York).

For example the compounds of formula (II) wherein X and Y are identical and represent an oxygen atom, and are thus the O,O-diesters of dithiophosphoric acid, can be prepared by reaction of compounds of an alcohol function with phosphorus pentasulphide. Primary or secondary aliphatic alcohols or phenols are generally used.

Illustrative alcohols includes n-propanol, isopropanol, n-butanol, isobutanol, n-pentanol, isopentanol, hexanol, ethyl-2-hexanol, methyl-4-pentanol-2, heptanol, n-octanol, teroctanol, nonanol, decanol, cyclohexanol, methylcyclohexanol, phenol, methoxyphenol, butylphenol, nonylphenol, or dodecylphenol.

Additional alcohols including the monoethers of glycol such as methoxy-2-ethanol, ethoxy-2-ethanol, or CELLOSOLVE® butoxy-2-ethanol, or the polyethoxylated alcohols such as those sold by RHONE-POULENC under the name of CEMULSOL®.

By using a 1,2 or 1,3-glycol, there is obtained a heterocycle having 5 or 6 links which contains phosphorus.

The compounds of formula (II) wherein X and Y are identical, represent a sulphur atom and thus the S,S-diesters of tetrathiophosphoric acid are obtained by reaction of mercaptans or of thiophenols with phosphorus pentasulphide. Among these compounds, there can be mentioned the propanethiol, the butanethiol, the isobutanethiol, the octanethiol, the dodecanethiol, or the thiophenol.

The compounds of formula (II) wherein X and Y are identical, represent a methylene group and thus the dialkyldithiophosphinic acids can be obtained from halides of thiophosphinic acid by reaction with sodium acid sulphide (NaHS) or from secondary phosphides or elementary sulphur. The diaryldithiophosphinic acids are prepared with excellent yields from aromatic compounds such as benzene and phosphorus pentasulphide in the presence of a catalyst of the FRIEDEL and CRAFTS type.

Within the scope of the invention, there are advantageously used compounds of formula (II) wherein X and Y are identical and represent an oxygen atom.

The S-alkylthiosulphates of the general formula (III) can be prepared by any known method. Thus, U.S. Pat. No. 2,004,873 describes the synthesis by chlorosulphonation of an alkyl mercaptan. U.S. Pat. No. 4,191,702, which is assigned to the same assignee as the present invention, describes the synthesis of the S-alkylthiosulphates by substitution of a thiosulphate ion for an alkyl halide in a biphasic system.

For the preparation of the compounds of general formula (I), it is particularly advantageous to prepare the S-alkylthiosulphate in a two phase system of water and organic solvent, in the presence of a phase transfer agent and without isolating it, to add the compound of formula (II).

It is not necessary to isolate the compound II previously, since it can be used in the form of a synthesis solution. In this case, the organic solvent containing compound II is added to the two phase system which contains the S-alkylthiosulphate and a phase transfer agent.

The temperature of the reaction can change widely, for example, between about 5° and about 150° C. but in general, temperatures on the order of from about 40° to about 90° C are sufficient.

The period of reaction is generally very short and does not exceed from about 10 minutes to about 5 hours.

By phase transfer agent is understood, without limitation to them, all the products capable of forming ligands with alkaline or alkaline earth metals such as the crown ethers and the quaternary ammonium and phosphonium salts described by DOCKS (Synthesis 8, 141 (1973)) or those described by E. V. DEHMLOW (Angew. International Chemistry, edition 13, (3) 170 (1974)) such as the trimethylbenzylammonium and triethylbenzyl ammonium chlorides, the tributylhexadecylphosphonium bromide, the dimethylphenyldodecylammonium chloride and the choline chloride.

The ion-exchanger resins on which are grafted the quaternary ammoniums can be likewise used.

The phase transfer agent is used at a concentration between about 0.2 and about 10% molar in relation to the compounds of general formula II and preferably from about 0.5 to about 8% molar.

As an organic solvent, there are used solvents which are not miscible in water and which dissolve the compounds of general formulae I and II. There can be mentioned methylene chloride or also the aromatic solvents such as toluene, chlorobenzene and the xylenes.

The additives according to the invention are incorporated into the lubricants of petroleum or synthetic origin. Among the synthetic lubricants can be enumerated the glycols, the ethers and esters of glycols, the polyalkylene glycols and the ethers and esters thereof and the esters of monocarboxylic or polycarboxylic acids and the monoalcohols and polyalcohols.

These are in general incorporated into the lubricating oils in amounts from about 0.1 to about 10% by weight of an additive. From about 0.1 to about 5% by weight is in general sufficient. These percentages correspond to a sulphur content of about 0.02 to about 4%.

The additives according to the invention can be used in combination with the other usual additives for lubricating oils such as the traditional detergent-dispersants like the alkylaryl sulphonates and the sodium, calcium, or magnesium alkyl phenates and/or the dispersants like the succinic derivatives or antioxidants such as the substituted phenols or the aromatic amines.

The antiwear power of the additives according to the invention is determined by means of a 4-ball machine by measuring the diameters of the marks of wear of the stationary balls. The antioxidant power of the additives is determined by the temperature at the beginning of the oxidation of a lubricating oil making use of the differential calorimetric analysis.

The performances of these additives under the simultaneous action of an oxygen pressure and of the temperature are measured by the oxidation, in the presence of catalysts, of a thin film of oil according to the method ASTM D-2277.

The examples that follow illustrate the invention without limiting it.

EXAMPLE 1

Preparation of the benzyldi(di n pentylthiophosphoryl)-bisulphide

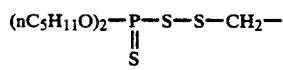

(a) to a suspension of $P_2S_5$ (14.7 g, 0.066 mole) in 30 ml toluene kept at 90° C., there are added in 30 minutes 23.3 g (0.26 mole) of n-pentanol previously dried on $CaCl_2$. The suspension is heated at the same temperature until the mixture becomes homogeneous.

(b) 12.66 g (0.1 mole) benzyl chloride dissolved in 50 ml. toluene are reacted with 34.9 g (0.14 mole) pentahydrated sodium thiosulphate and 1.12 g (0.008 mole) choline chloride dissolved in 20 ml water. The contents of the reactor are mechanically stirred for 4 hours, the temperature being kept at 70°–80° C.

(c) the solution prepared in 1a is added to the solution prepared in 1b over a period of about 15 minutes while maintaining the temperature at 60°–70° C. After cooling, the organic phase is washed 3 times, then dried on $Na_2S_2O_4$. After evaporation of the solvent, the product is eluted under a silicon column using as an eluant, a pentane-ether mixture (2000 ml, 95/5). To the solution thus obtained, there is added, while vigorously stirring, 200 ml of a solution saturated with $Na_2CO_3$. After drying the organic phase, the solvents are evaporated and there are recovered 36.8 g of a yellow oil (yield 94%).

Calculated analysis C 52.0., H 7.45, P 7.89, S 24.37. Found C 52.19, H 7.87, P 7.83, S 24.8.

RMN: $^{31}P$ not disengaged 89.3 ppm, quintuplet $3J_{P-H^-}$ 9,2 Hz

EXAMPLE 2

Preparation of the benzyl (diisopropylthiophosphoryl) bisulphide

The procedure is carried out as in Example 1, but replacing the 23.3 g (0.26 mole) n-pentanol by 15.6 g (0.26 mole) isopropanol. The product is obtained in the form of a yellow oil (31 g, yield 92%).

Calculated analysis C 46.41, H 5.29, P 9.21. Found C 45.10, H 5.31, P.

RMN: $^{31}P$ disengaged 86.4 ppm.

RMN: $^{13}C$ (ppm): 23.6, 42.9, 73.7, 127.6, 128.4, 129.3, 135.7.

EXAMPLE 3

Preparation of the allyl (di-n-pentylthiophosphoryl) bisulphide

The procedure is carried out as in Example 1, but replacing the 12.66 g benzyl chloride by 7.665 (0.1 mole) allyl chloride. The product is obtained in the form of a yellow liquid with a yield of 90%.

EXAMPLE 4

The procedure is carried out as in Example 1, but replacing 23.3 g (0.26 mole) n-pentanol by 23.3 g (0.26 mole) isoamylic alcohol. The benzyl (diisoamylthiophosphoryl) bisulphide is obtained with a yield of 91%.

EXAMPLE 5

Comparison: Without Phase Transfer Agent (a) there is prepared 0.132 mole diisopropyldithiophosphoric acid from 14.7 g (0.066 mole) $P_2S_5$ in 30 ml toluene to which are added in 30 minutes 15.6 g (0.26 mole) isopropylic alcohol. The solution is heated at 90° C. during the addition of the alcohol and is kept at this temperature until the mixture becomes homogeneous.

(b) 12.66 g (0.1 mole) benzyl chloride are made to react in 50 ml ethanol with 34.9 g (0.14 mole) of pentahydrated sodium thiosulphate previously dissolved in 50 ml water. The contents of the reactor are kept under stirring for 8 hours with reflux of the solvent. After the end of the reaction, the solvent is evaporated and the benzyl thiosulphate is collected in the form of a white powder.

(c) the solution in the toluene of the diisopropyldithiophosphoric acid prepared in 5a is brought into contact with the benzyl thiosulphate prepared in 5b and previously dissolved in 50 ml water. The aggregate is heated for 1 hour while keeping the temperature at 65°–70° C. After evaporation of the solvent and purification according to Example 1a, there are recovered 20.2 g of product (Rt=60%).

EXAMPLE 6

The antiwear power of the lubricating composition, containing as basic oil the mineral oil 200 Neutral Solvent and as the additive, a product of the invention, has been determined by means of the 4-ball machine EP of SHELL the description of which appears in "Annual BOOK OF ASIM STANDARDS" Part 24, pages 680–688, 1979. The test consists in rotating a ball of 12 mm diameter at a speed of 1500 tr/mn on three other balls kept stationary and coated with lubricant. A load of 40 or 60 daN is applied by a lever system which pushes the 3 stationary balls toward the upper ball situated in a mandrel.

The antiwear effectiveness of a lubricant is determined by the medium value of the diameter of the marks of wear on the three stationary balls after one hour of operation. The lubricating compositions have been tested in a manner such that the sulphur content brought by the additives is equal to 0.4%.

| PRODUCT | % PRODUCT IN OIL 200N | 0 mm 40 daN | 0 mm 60 daN |
|---|---|---|---|
| — | — | 1.5 | 2.2 |
| Example 1 | 1.63 | 0.46 | 0.91 |
| Example 2 | 1.4 | 0.48 | 1.28 |
| Example 3 | 1.42 | 0.45 | 0.87 |
| Example 4$^x$ | 1.63 | 0.49 | 0.95 |

| PRODUCT | % PRODUCT IN OIL 200N | 0 mm 40 daN | 0 mm 60 daN |
|---|---|---|---|
| Example 4[xx] | 1.63 | 0.49 | 0.74 |

[x]product after purification
[xx]raw product not purified

EXAMPLE 7

In this example, the antioxidant power of the additives of the invention is determined by dynamic oxidation using the differential calorimetric analysis with a programming of rise in temperature of 5° C./mn and a supply of air of 10 l/h. Thus is determined the temperature at the beginning of oxidation of the oil.

| oil 200N | T beginning of oxidation 155° C. |
|---|---|
| oil 200N + 1% example 1 | = 208° C. |
| oil 200n + 1% Lz 1395 | = 195° C. |

Lz 1395 is a zinc dithiophosphate prepared from branched alcohols (% S - 19%).

EXAMPLE 8

In this example, the performances of the lubricating compositions of the invention are determined under the simultaneous action of an oxygen pressure and of the temperature according to the method TFOUT (thin film oxidation uptake test), ASTM D 2272. The oxidation is effected in the presence of catalysts and on a thin film of oil. There is determined the time of induction that precedes the drop of oxygen pressure in the autoclave (the more elevated the time of induction, the more antioxidant the products are).

| oil 200N | Ti = 20 mn |
|---|---|
| oil 200N + 1.4% example 2 | Ti = 160 mn |
| oil 200N + 1.2% example 4 | Ti = 1810 mn |
| oil 200n + 1.2% Lz 1395 | Ti = 140 mn. |

What is claimed is:

1. A process for the preparation of dithiophosphorous disymmetric bisulfide of the formula:

(I)

wherein X and Y can be identical or different, and represent an oxygen or sulphur atom or a methylene group, with the provisos that:

(a) if X and Y represent an oxygen or sulphur atom, $R_1$, $R_2$ and $R_3$ can be identical or different and represent a hydrocarbon acyclic or cyclic, saturated, unsaturated or aromatic radical or a chain of the general formula:

wherein $Z_1$ and $Z_2$, can be identical or different, and correspond to an oxygen or sulphur atom, $R_4$ corresponds to an alkyl group, $R_5$ corresponds to an alkylene group and is an between 0 and 8, and (b) if X and Y represent a methylene group, $R_1$ and $R_2$, can be identical or different, and represent a hydrogen atom or a hydrocarbon radical and $R_3$ represents a hydrocarbon radical, said process comprising condensing a compound of the general formula:

(II)

with an S-alkylthiosulphate of the general formula

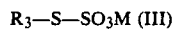

(III)

in a two phase medium containing water and an organic solvent in the presence of a phase transfer agent, wherein $R_1$, $R_2$, $R_3$, X and Y are as indicated and M represents an alkaline or alkaline earth metal or an ammonium ion.

2. The process according to claim 1, wherein the organic solvent is methylene chloride, or an aromatic solvent selected from the group consisting of toluene, chlorobenzene and the xylenes.

3. The process according to claim 1, wherein the phase transfer agent is used in a concentration between about 0.2 and about 10% molar in relation to compounds of the general formula (II).

4. A process according to claim 3 wherein the phase transfer agent is used in a molar concentration between about 0.5 and 8%.

5. A process according to claim 1 wherein the reaction temperature varies between about 5° and 150° C., and the period of reaction varies between about 10 minutes and about 5 hours.

6. A process according to claim 5 wherein the reaction temperature varies between about 40° and 90° C.

* * * * *